(12) United States Patent
Hotchkiss et al.

(10) Patent No.: US 8,323,281 B2
(45) Date of Patent: Dec. 4, 2012

(54) EXTERNAL FIXATION DEVICES AND METHODS OF USE

(75) Inventors: Robert N. Hotchkiss, Riverside, CT (US); Joseph Lipman, New York, NY (US); Darrick Lo, Greenbrook, NJ (US)

(73) Assignee: The Hospital for Special Surgery, New York, NY (US)

( * ) Notice: Subject to any disclaimer, the term of this patent is extended or adjusted under 35 U.S.C. 154(b) by 64 days.

(21) Appl. No.: 12/712,188

(22) Filed: Feb. 24, 2010

(65) Prior Publication Data

US 2010/0249779 A1 Sep. 30, 2010

Related U.S. Application Data

(60) Provisional application No. 61/154,849, filed on Feb. 24, 2009.

(51) Int. Cl.
*A61B 17/60* (2006.01)
(52) U.S. Cl. .......................... 606/59; 606/54
(58) Field of Classification Search .............. 606/53–59, 606/86 B, 105
See application file for complete search history.

(56) References Cited

U.S. PATENT DOCUMENTS

| | | | | |
|---|---|---|---|---|
| 4,621,627 A | * | 11/1986 | DeBastiani et al. | 606/57 |
| 5,100,403 A | | 3/1992 | Hotchkiss et al. | |
| 5,941,877 A | * | 8/1999 | Viegas et al. | 606/55 |
| 6,152,925 A | | 11/2000 | Marsh et al. | |
| 6,162,223 A | * | 12/2000 | Orsak et al. | 606/59 |
| 6,217,577 B1 | * | 4/2001 | Hofmann | 606/57 |
| 6,520,961 B1 | * | 2/2003 | Marsh | 606/54 |

OTHER PUBLICATIONS

Tan, V. et al., "Hinged Elbow External Fixators: Indications and Uses," Journal of the American Academy of Orthopaedic Surgeons, vol. 13, No. 8, Dec. 2005, pp. 503-514.
Ring, D. et al., "Hinged Elbow External Fixation for Severe Elbow Contracture," J. Bone Joint Surg. Am. 2005; 87: 1293-1296.
"OptiROM Elbow Fixator—Surgical Technique," Biomet Trauma, 2008, pp. 1-25.
"Elbow Fixator," Orthofix, 2009, http://www.orthofix.com/products/elbowfixator.asp?cid=16.
"Elbow Fixator—Early Mobilization in Fractures and Fracture-Dislocations of the Elbow Joint," Brochure—Orthofix, Nov. 2006.
Tucker, J. "Compass Universal Hinge," Knee Surgical Technique, 2000, pp. 1-15.
"Stryker Dynamic Joint Distractor II," Stryker, http://www.stryker.com/en-us/products/Trauma/UpperExtremityHand/Elbow/DJDII/index.htm#, Copyright 1998-2008.
"OptiROM Elbow," Biomet, Inc, 2009.

* cited by examiner

*Primary Examiner* — Pedro Philogene
(74) *Attorney, Agent, or Firm* — Leason Ellis LLP (57) ABSTRACT

External fixation devices and methods of use are provided. A device for external fixation of a joint includes a first pin block for connection to a first skeletal element and a second pin block for connection to a second skeletal element. The device includes a connection assembly that is releasably attached to at least one of the pin blocks. The device is locked in an original position when the connection assembly is attached to both of the pin blocks, and is unlocked when the connection assembly is detached from at least one of the pin blocks.

28 Claims, 10 Drawing Sheets

EXTERNAL FIXATION DEVICES AND METHODS OF USE

CROSS-REFERENCE TO RELATED APPLICATION

This application claims priority under 35 U.S.C. §119(e) to U.S. Provisional Application Ser. No. 61/154,849, filed on Feb. 24, 2009, which is hereby incorporated by reference herein in its entirety.

BACKGROUND

Current external fixation technology includes two main groups of devices: static fixation systems and hinged fixation systems. Static external fixation has been used in the upper limb for decades, including the elbow. A drawback with static external fixation is that the joint becomes stiff without motion. The fixator systems for static application can also be difficult to dismantle and reassemble for post-operative mobilization. Therefore, once applied, these static fixation systems can lead to more stiffness and suboptimal results.

Existing hinged devices include a single joint axis that can be unlocked so that the arm can be flexed and extended while the external fixator remains connected to the humerus and ulna. These external hinged devices are challenging to apply and, unless used on a frequent basis, can require long operative time. In order to match the hinge axis of the fixator to the hinge axis of the elbow joint, fluoroscopy is used, or a pin is driven directly through the axis of the joint. It is difficult to precisely place this axis. If the alignment is suboptimal, the device may bind and lead to more limited motion or worse, joint subluxation. In an emergency setting, the requisite skilled personnel and equipment may not be available. The complexity of these devices leads to a general reluctance to use them, even in patients that require some form of external fixation. This can result in inadequate treatment, secondary referrals, and/or subsequent poor outcomes.

Accordingly, it would be desirable to provide a device that allows for a simplified device application and the ability to maintain joint motion.

SUMMARY

External fixation devices and methods of use are provided.

In some embodiments, a device for external fixation of a joint is provided, the joint having an anatomic pivot axis about which first and second skeletal elements are disposed. The device includes a first pin block for connection to the first skeletal element, a second pin block for connection to the second skeletal element, and a connection assembly for connection to the first and second pin blocks. The connection assembly is releasably attached to at least one of the first and second pin blocks to allow the device to be locked in an original position when the connection assembly is attached to the first and second pin blocks, and to allow the device to be unlocked when the connection assembly is detached from at least one of the first and second pin blocks.

In one example, the connection assembly includes first and second end portions coupled to the first and second pin blocks, and a linking member extending between and connected to the first and second end portions. The connections between the linking member and the first and second end portions each include a fastener to maintain the linking member in a fixed position with respect to the first and second pin blocks, and at least one of the connections is a releasable attachment. The releasable attachment between the linking member and the at least one of the first and second end portions may include, for example, at least one screw configured to remain engaged to at least one of the first and second end portions following the release of the linking member from the at least one of the first and second end portions.

In another example, the joint is rigidly constrained when the device is locked. In yet another example, the joint may be constrained to translate on a plane defined by the surface of the linking member and rotate about an axis perpendicular to the plane when the device is unlocked. The device is unlocked when the linking member is detached from one of the first and second end portions. In still another example, the joint is unconstrained when the device is unlocked, the device being unlocked when the linking member is detached from the first and second end portions.

In yet another example, the linking member is configured to accommodate a plurality of distances between the first and second pin blocks. For example, the linking member may include a plurality of locking sites to accommodate the plurality of distances between the first and second pin blocks. In still another example, at least one of the first and second end portions may include a plurality of locking sites to which one of the plurality of locking sites of the linking member is releasably attached. The linking member may be configured for reattachment to at least one of the first and second end portions at a selected locking site so that the device is locked in the original position.

In still another example, the connection assembly includes first and second end portions each releasably coupled to the first and second pin blocks, respectively, by a locking mechanism, and a linking member extending between and rotatably connected to the first and second end portions. The rotatable connections between the linking member and the first and second end portions may be configured to maintain the linking member in a fixed position with respect to the first and second pin blocks when the device is locked. The linking member may include an expandable linking member adapted to accommodate the distance between the first and second pin blocks. In another example, the linking member may include a first curved member in sliding engagement with a second curved member, the sliding engagement between the first and second curved members allowing the linking member to adjust in size to accommodate the distance between the first and second pin blocks.

In yet another example, the linking member may include a plurality of modular linkages to accommodate the distance between the first and second pin blocks. In still another example, the rotatable connections between the linking member and the first and second end portions may include spherical ball joints. In yet another example, the first and second end portions may be adapted for translation and rotation with respect to the first and second pin blocks.

In some embodiments, a device for external fixation of a joint is provided, the joint having an anatomic pivot axis about which first and second skeletal elements are disposed. The device includes a first pin block for connection to the first skeletal element, a second pin block for connection to the second skeletal element, and a connection assembly for connection to the first and second pin blocks. The connection assembly includes first and second end portions coupled to the first and second pin blocks and a linking member extending between and connected to the first and second end portions. The connections between the linking member and the first and second end portions each include a fastener to maintain the linking member in a fixed position with respect to the first and second pin blocks. The linking member is releasably attached to one of the first and second end portions to allow the device to be locked in an original position when the linking member is attached to the first and second pin blocks, and to allow the device to be unlocked when the linking member is detached from one of the first and second end portions. The joint is rigidly constrained when the device is locked, and the joint is constrained to translate on a plane defined by the surface of the linking member and rotate about an axis perpendicular to the plane when the device is unlocked. The linking member is configured to reattach to one of the first and second pin blocks to lock the device in the original position.

In one example, the linking member includes a plurality of locking sites to accommodate the distance between the first and second pin blocks. In another example, the linking member is configured to prevent one of the first and second end portions from rotating into the plane formed by the linking member when the device is unlocked.

In some embodiments, a device for external fixation of a joint is provided, the joint having an anatomic pivot axis about which first and second skeletal elements are disposed. The device includes a first pin block for connection to the first skeletal element, a second pin block for connection to the second skeletal element, and a connection assembly for connection to the first and second pin blocks. The connection assembly includes first and second end portions each releasably attached to the first and second pin blocks, respectively, by a locking mechanism to allow the connection assembly to be released from the first and second pin blocks, and a linking member extending between and rotatably connected to the first and second end portions. The rotatable connections between the linking member and the first and second end portions are each configured to maintain the linking member in a fixed position with respect to the first and second pin blocks. The connection assembly is releasably attached to the first and second pin blocks to allow the device to be locked in an original position when the connection assembly is attached to the first and second pin blocks, and to allow the device to be unlocked when the connection assembly is detached from the first and second pin blocks. The joint is rigidly constrained when the device is locked, and the joint is unconstrained when the device is unlocked. The connection assembly is configured to reattach to the first and second pin blocks to lock the device in the original position.

In one example, the linking member comprises a first curved member in sliding engagement with a second curved member, the sliding engagement between the first and second curved members allowing the linking member to adjust in size to accommodate the distance between the first and second pin blocks. In another example, the linking member comprises a plurality of modular linkages to accommodate the distance between the first and second pin blocks.

In accordance with the disclosed subject matter, external fixation devices and methods of use are provided.

DETAILED DESCRIPTION

An external fixation device and methods of use are provided.

The fixation device disclosed herein allows for a simplified device application and the ability to maintain joint motion. The device can be easily removed for rehabilitation and reapplied for protection of the joint when not under supervision or in the protected mobilization position. The fixation device and methods of use may require less training and operative time, while still supporting joint alignment during healing of the joint (e.g., a four to six week period). The device may have a lower profile than existing devices, making the device easier for a patient to manage during activities of daily living.

In some embodiments, the external fixation device may include a "simple-release" locking mechanism, making it easier for a surgeon or physical therapist to remove the rigid elbow constraint (e.g., a variable-linkage assembly), actively move the joint through a safe range of motion, and return the elbow to a rigid state by reapplying the constraint. The use of the device may protect the elbow from, for example, subluxation.

In some embodiments, the fixator assembly may rigidly fix the humerus with respect to the ulna in a patient. At surgery, the elbow can be locked in a flexed position ranging, for example, from 30-120° when joint congruency is properly attained. The elbow can be locked in the flexed position using, for example, a variable-linkage assembly as disclosed herein.

The following FIGS. 1-5 and their accompanying descriptions provide detailed examples of the implementation of the devices and methods disclosed herein.

Figure 1A:
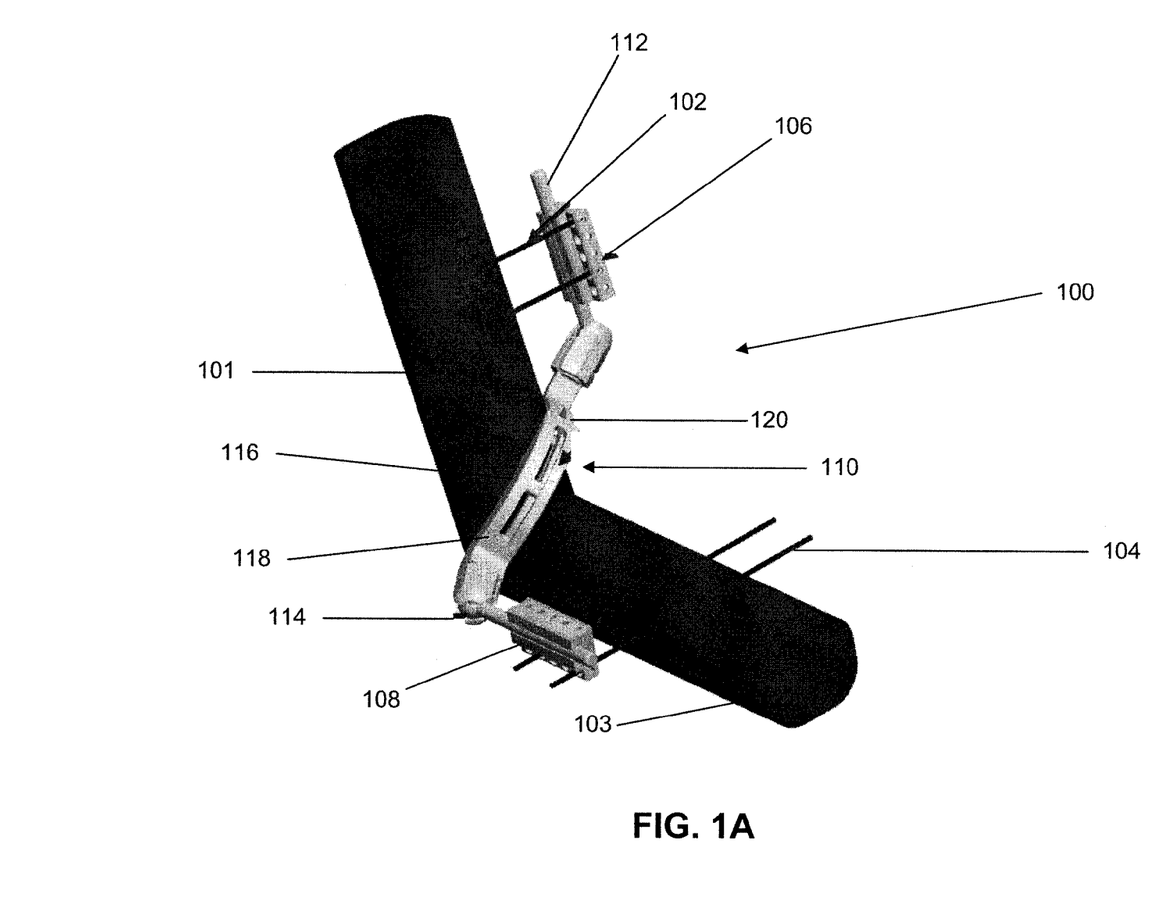
FIG. 1A is a perspective view of an illustrative external fixator assembly in accordance with some embodiments of the disclosed subject matter.
Figure 1B:
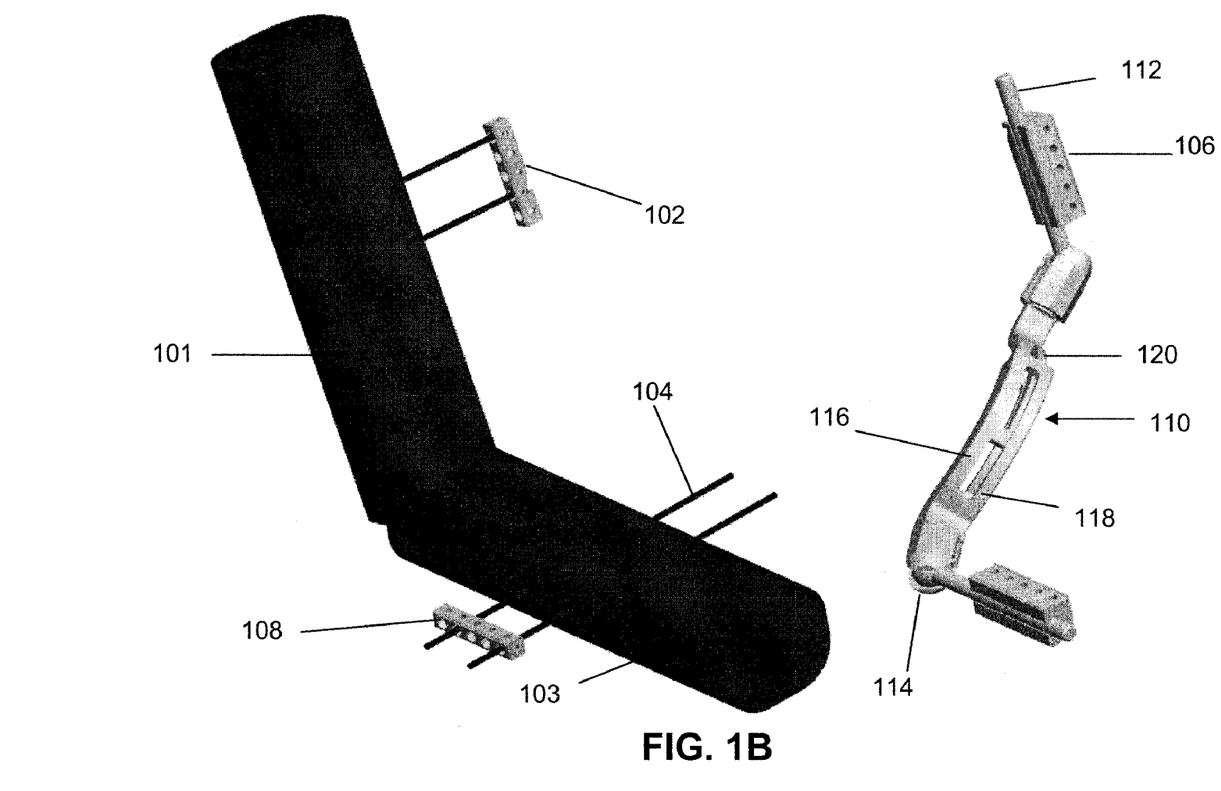
FIG. 1B is a perspective view of the external fixator assembly shown in FIG. 1A as detached from the pin blocks in accordance with some embodiments of the disclosed subject matter.

FIG. 1A is a perspective view of an illustrative external fixator assembly in accordance with some embodiments of the disclosed subject matter. FIG. 1B is a perspective view of the external fixator assembly shown in FIG. 1A as detached from the pin blocks in accordance with some embodiments of the disclosed subject matter. As shown in FIGS. 1A-1B, fixator assembly 100 connects from the medial aspect of humerus 101 to the postero-lateral aspect of ulna 103. This positioning is merely illustrative, and fixator assembly 100 may be positioned in any other suitable manner in accordance with the disclosed subject matter.

Fixator assembly 100 includes bone pins 102, 104, pin blocks 106, 108, and variable-linkage assembly 110. As shown in FIGS. 1A-1B, at least two bone pins 102 are placed into humerus 101, and at least two bone pins 104 are placed into ulna 103. This is merely illustrative, and any suitable number of bone pins may be used in accordance with the disclosed subject matter. In some embodiments, the bone pins may include a threaded region that is conical in shape and coated, for example, with hydroxyapatite. A comparable pin is provided, for example, by Orthofix. When placing pins 102 in humerus 101, the midshaft of humerus 101 where the radial nerve resides should be avoided.

A pin block 106 may be used to capture the set of humeral pins 102 and a pin block 108 may be used to capture the set of ulnar pins 104. The pin blocks 106, 108 are capable of capturing bone pins that are not in parallel with each other. Once captured, pin blocks 106, 108 rigidly lock a bone pin with respect to its adjacent pin or pins. An example of a pin block currently on the market is a Rancho block. While standard Rancho blocks are referred to herein, it should be noted that this is just one example of a pin block for use with the disclosed external fixator assembly, and the embodiments described herein can be used with any other suitable pin block. Alternatively, the embodiments disclosed herein may be used with any other suitable mechanism for affixing the assembly to the bones of a patient.

As shown in FIGS. 1A-1B, variable linkage assembly 110 connects to humeral and ulnar pin blocks 106, 108, respectively, by means of locking mechanisms (not shown). Locking mechanisms may be referred to, for example, as "simple release" locking mechanisms, and can include devices such as pins, screws or bolts. Alternatively, the embodiments described herein can be used with any other suitable locking mechanism.

Variable linkage assembly 110 includes two spherical joints 114, two rotatable and translatable arms 112, and a curved slider 116 that wraps around the anterior aspect of the elbow joint. The variable linkage assembly as illustrated in FIGS. 1A and 1B provides a total of 11 degrees of freedom for the elbow joint. The combination of elements in linkage assembly 110 is merely illustrative, and any suitable combination of elements can be used to result in the same or different number of degrees of freedom in accordance with the disclosed subject matter. Curved slider 116 is coupled at both ends to arms 112 by spherical joints 114, and arms 112 are coupled to humeral and ulnar pin blocks 106, 108 by locking mechanisms. Spherical joints 114 allow arms 112 to be rotatable to accommodate, for example, the positioning and orientation of pin blocks 106, 108. In order to create a rigid construct of fixator assembly 100, spherical joints 114 can be rigidly locked in place (e.g., with set screws). Because spatial position of pins 102 and 104 can vary from one patient to the next, variable linkage assembly 110 is designed with enough degrees of freedom to accommodate any pin orientation within surgical reason (e.g., surgical safe zones). For example, in the embodiment shown in FIGS. 1A-1B, curved slider 116 includes two curved members 118, 120 that are in sliding engagement with each other so that curved slider 116 can be lengthened or shortened by sliding curved member 118 with respect to curved member 120.

At time of rehabilitation, a surgeon or physical therapist can release variable-linkage assembly 110 at the locking mechanisms to allow the patient to flex and extend his/her elbow. In some embodiments, rigidly locked variable-linkage assembly 110 can be released from the locking mechanisms at pin blocks 106, 108. When variable-linkage assembly 110 is released from pin blocks 106, 108, the joint is unconstrained and may be mobilized in any direction. For example, the joint may be mobilized in a protected, supervised program by the surgeon or physical therapist. When the joint needs to be stabilized again, variable-linkage assembly 110 is reattached to pin blocks 106, 108 in the original position obtained in the operating room using locking mechanisms.

In some embodiments, the locking mechanisms may include one or more screws that are captured so that they do not fall out of fixator assembly 100 when variable-linkage assembly 110 is detached from pin blocks 106, 108. In some embodiments, fixator assembly 100 may be clearly labeled and designed such that the therapist or patient is only able to release the locking mechanisms and not loosen other joints in variable linkage assembly 110. This may be done, for example, by color coding the screws of the locking mechanisms. In another example, a different drive design for the locking mechanisms may be used. For example, an Allen hex recess may be used for the screws in the locking mechanisms, and triangular-headed screws may be used for the joints of variable-linkage assembly 110 to prevent tampering. These examples are merely illustrative, and any suitable feature or combination of features may be used to prevent tampering with the variable linkage assembly 110.

Figure 2:
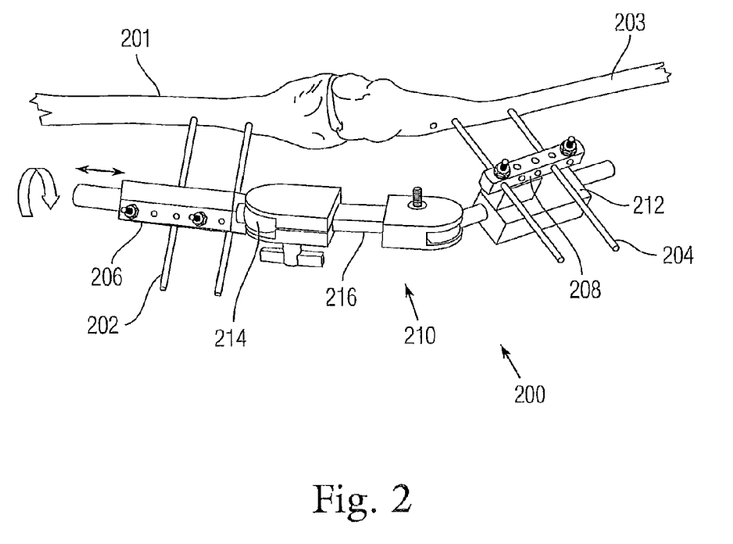
FIG. 2 is a perspective view of another illustrative external fixator assembly in accordance with some embodiments of the disclosed subject matter.

FIG. 2 is a perspective view of another illustrative external fixator assembly in accordance with some embodiments of the disclosed subject matter. As shown in FIG. 2, external fixator assembly 200 connects the postero-lateral aspects of both humerus 201 and ulna 203. This positioning is merely illustrative, and fixator assembly 200 may be positioned in any other suitable manner in accordance with the disclosed subject matter.

Fixator assembly 200 includes bone pins 202, 204, pin blocks 206, 208, and variable-linkage assembly 210. Bone pins 202, 204 and pin blocks 206, 208 may be positioned on and attached to both humerus 201 and ulna 203 in the same fashion as shown in the embodiment of FIG. 1. Variable linkage assembly 210 may be releasably coupled to humeral and ulnar pin blocks 206, 208 by locking mechanisms in the same fashion as shown in the embodiment of FIG. 1.

As shown in FIG. 2, variable linkage assembly 210 includes connector 216, two spherical joints 214, and two rotatable and translatable arms 212. The variable linkage assembly as illustrated in FIG. 2 provides a total of 10 degrees of freedom for the elbow joint. The combination of elements in linkage assembly 210 is merely illustrative, and any suitable combination of elements can be used to result in the same or different number of degrees of freedom in accordance with the disclosed subject matter.

Arms 212 of linkage assembly 210 are releasably coupled at one end to pin blocks 206, 208 by locking mechanisms in the same fashion as shown in the embodiment of FIG. 1. Arms 212 are coupled at the other end to connector 216 by spherical joints 214 in the same fashion as shown in the embodiment of FIG. 1. Spherical joints 214 can be rigidly locked in place (e.g., with set screws) in the same fashion as shown in the embodiment of FIG. 1 to create a rigid construct of fixator assembly 200.

At time of rehabilitation, a surgeon or physical therapist can release variable-linkage assembly 210 from the locking mechanisms in the same fashion as shown in the embodiment of FIG. 1. In some embodiments, rigidly locked variable-linkage assembly 210 can be released from the locking mechanisms at pin blocks 206, 208 so that the joint can be unconstrained and mobilized in any direction. For example, the joint may be mobilized in a protected, supervised program by the surgeon or physical therapist. When the joint needs to be stabilized, variable-linkage assembly 210 is reattached to pin blocks 206, 208 in the original position obtained in the operating room using locking mechanisms. Fixator assembly 200 may be designed such that screws from the locking mechanisms are not lost when it is detached from pin blocks 206, 208, and such that elements of variable linkage assembly 210 are not tampered with, as described in connection with fixator assembly 100 of FIG. 1.

Figure 3A:
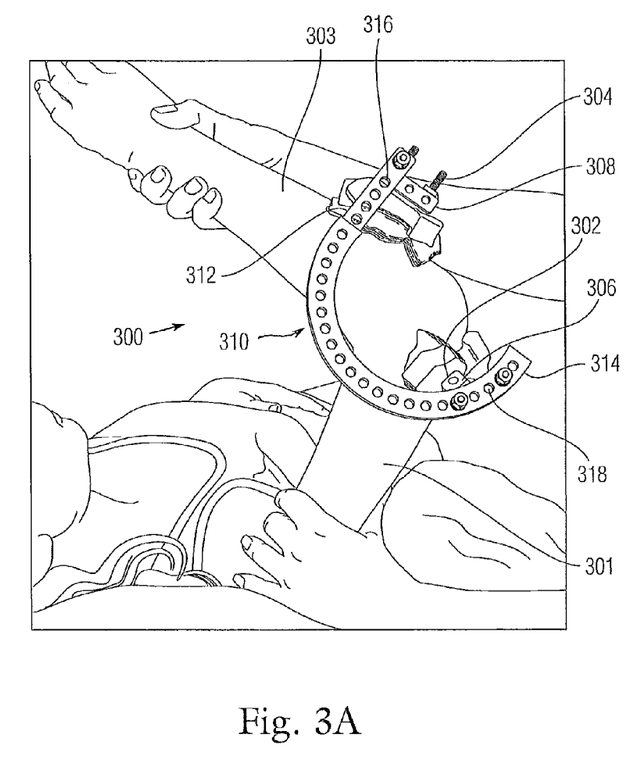
FIG. 3A is a perspective view of yet another illustrative external fixator assembly in accordance with some embodiments of the disclosed subject matter.

FIG. 3A is a perspective view of yet another illustrative external fixator assembly in accordance with some embodiments of the disclosed subject matter. As shown in FIG. 3A, external fixator assembly 300 connects the postero-lateral aspects of both humerus 301 and ulna 303. This positioning is merely illustrative, and fixator assembly 300 may be positioned in any other suitable manner in accordance with the disclosed subject matter.

Fixator assembly 300 includes bone pins 302, 304, pin blocks 306, 308, and variable-linkage assembly 310. Bone pins 302, 304 and pin blocks 306, 308 may be positioned on and attached to both humerus 201 and ulna 203 in the same fashion as shown in the embodiment of FIG. 1.

Figure 3B:
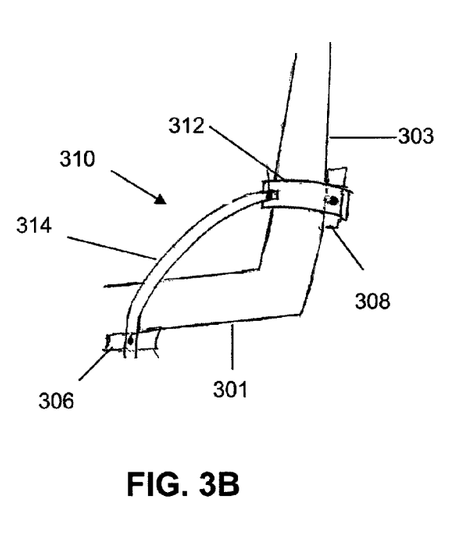
FIG. 3B is a perspective view of the external fixator assembly shown in FIG. 3A illustrating connecting arch as connected to both pin blocks in accordance with some embodiments of the disclosed subject matter.
Figure 3C:
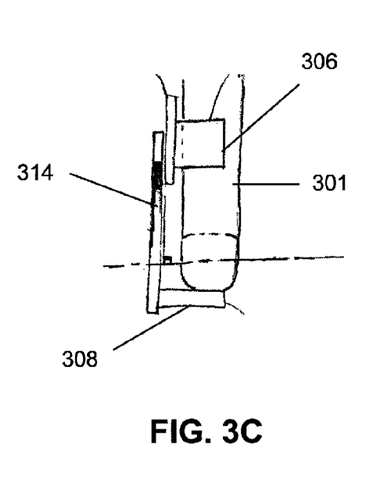
FIG. 3C is a perspective view of the external fixator assembly shown in FIG. 3A in accordance with some embodiments of the disclosed subject matter.

FIG. 3B is a perspective view of the external fixator assembly shown in FIG. 3A illustrating connecting arch as connected to both pin blocks in accordance with some embodiments of the disclosed subject matter. FIG. 3C is another perspective view of the external fixator assembly shown in FIG. 3A in accordance with some embodiments of the disclosed subject matter. As shown in FIGS. 3B-3C, variable-linkage assembly 310 includes arm member 312 and connecting arch 314. Arm 312 is rotatably coupled at one end to pin block 308 by a locking mechanism (not shown). Once a desired position and orientation is found approximately perpendicular to the axis of the joint, arm 312 may be locked into place. Connecting arch 314 is coupled at one end to pin block 306 and coupled at the other end to arm 312 by a fastener (not shown). In some embodiments, the fastener may be the same as the locking mechanism that couples arm 312 to pin block 308. In some embodiments, the fastener may be a different type of locking mechanism. As shown in FIG. 3A, arm 312 and connecting arch 314 may include multiple locking sites 316 and 318, respectively, that can be releasably engaged by the fastener in order to accommodate various spatial positions between pin blocks 306, 308. Connecting arch 314 may slide on the top surface of arm 312 until a desired position and orientation for variable-linkage assembly 310 is found. Once a desirable position and orientation is found, the fastener couples connecting arch 314 to arm 312 at respective locking sites 318, 316 to create a rigid construct of fixator assembly 300.

In some embodiments, variable-linkage assembly 310 may include two adjustable arms and a connecting arch (not shown). In such embodiments, one or both of the adjustable arms may be rotatably coupled to pin blocks 306, 308. The connecting arch may be releasably coupled at one or both ends to the adjustable arms by fasteners as described herein to create a rigid construct of the fixator assembly.

Figure 3D:
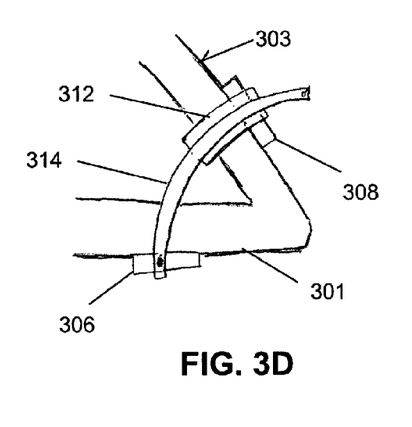
FIG. 3D is a perspective view of the external fixator assembly shown in FIG. 3A illustrating connecting arch as disconnected from the ulnar pin block in accordance with some embodiments of the disclosed subject matter.

FIG. 3D is a perspective view of the external fixator assembly shown in FIG. 3A illustrating connecting arch as disconnected from the ulnar pin block in accordance with some embodiments of the disclosed subject matter. As shown by FIG. 3D, a surgeon or physical therapist can release connecting arch 314 at the fastener and allow the patient to flex and extend his/her elbow. In some embodiments, at least one end of rigidly locked connecting arch is released from the fastener at arm 312. When connecting arch 314 is released from arm 312, the joint can be mobilized and is only constrained by the plane formed by connecting arch 314. This allows the elbow joint to have three degrees of freedom of movement because ulna 303 can translate on the plane of the surface of connecting arch 312, and it can rotate about an axis perpendicular to the plane. When the joint needs to be stabilized again, connecting arch 314 is reattached to arm 312 in the original position obtained in the operating room using the fastener.

In embodiments in which variable linkage assembly 310 includes two adjustable arms releasably coupled to a connecting arch at both ends, the connecting arch can be detached from both arms so that the joint is completely unrestrained and can be mobilized in any direction. Alternatively, and as described above, the connecting arch may be detached from only one arm such that the movement of the joint is constrained by the plane of the connecting arch.

Figure 4A:
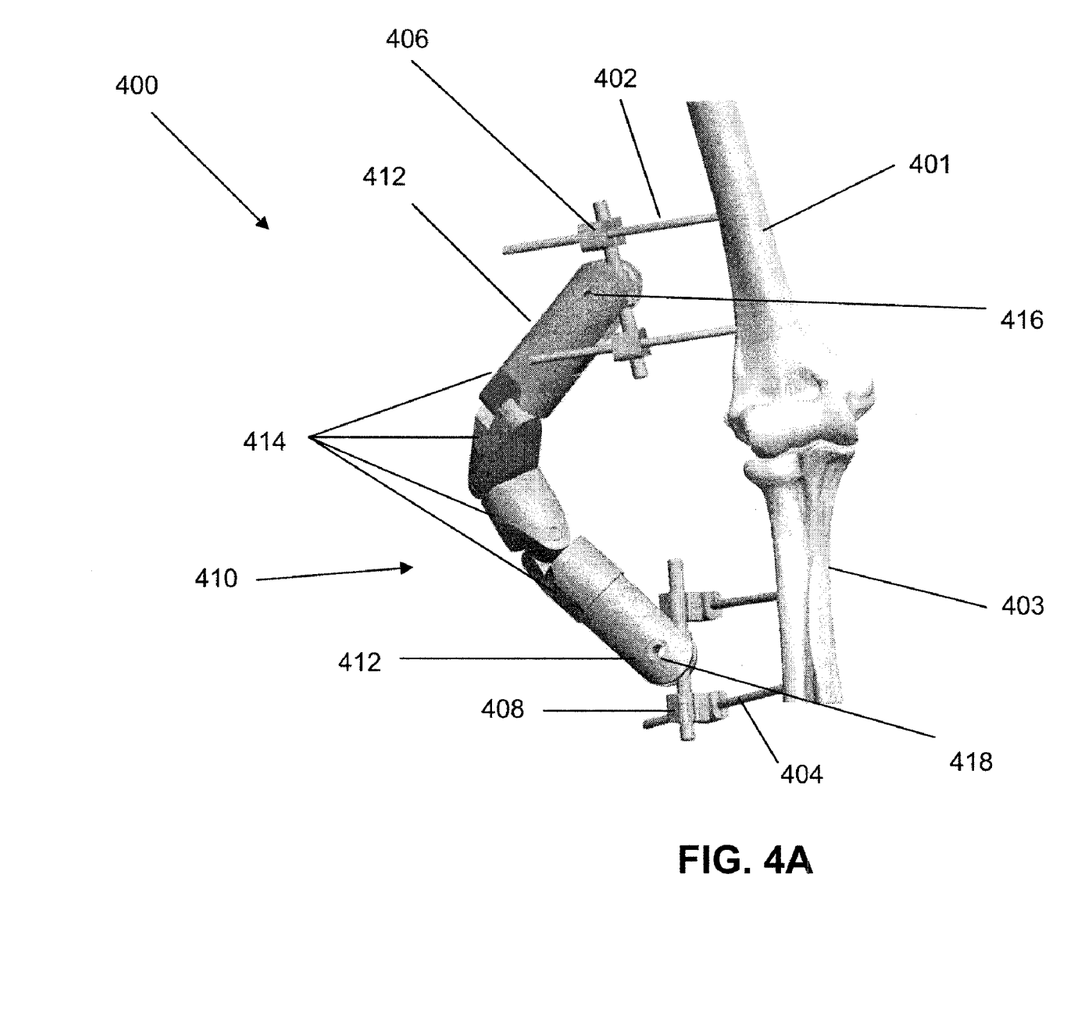
FIG. 4A is a perspective view of still another illustrative external fixator assembly in accordance with some embodiments of the disclosed subject matter.
Figure 4B:
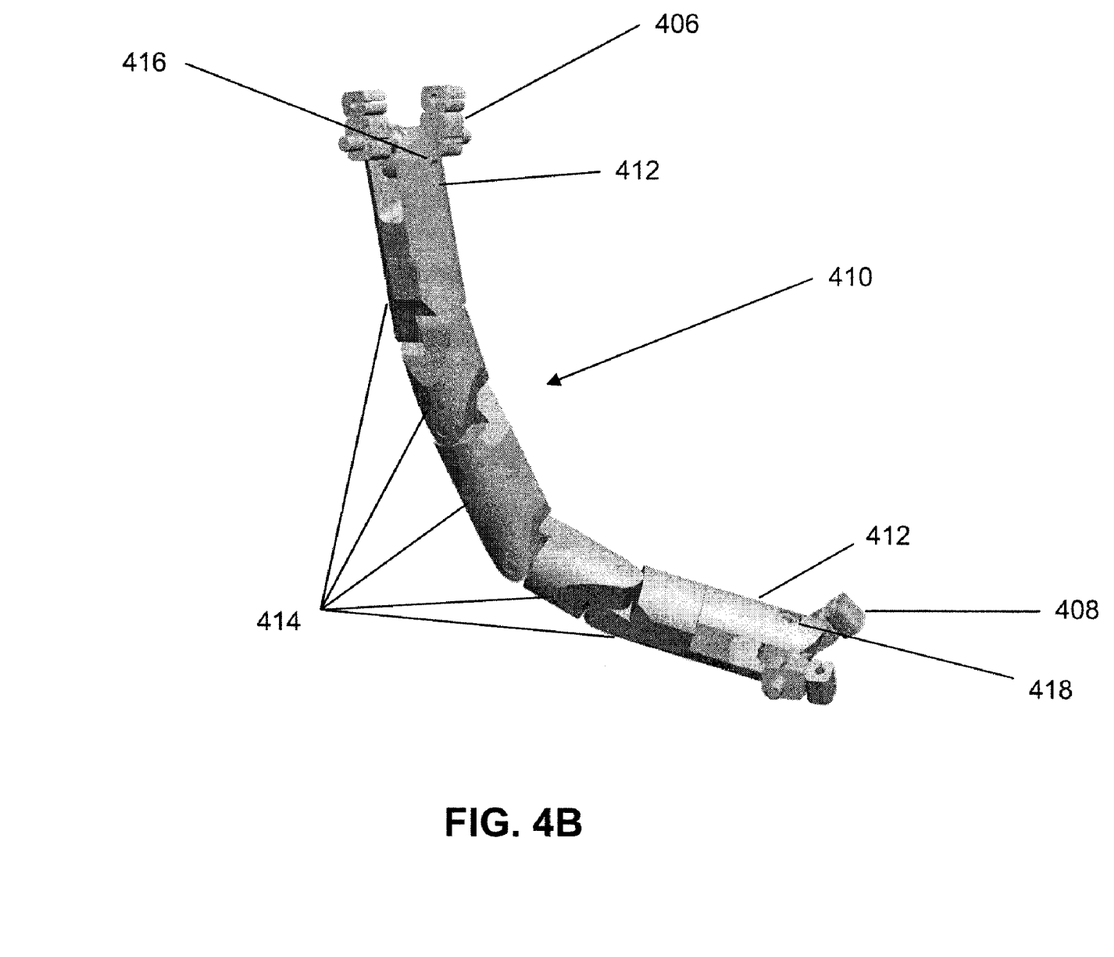
FIG. 4B is a perspective view of the external fixator assembly shown in FIG. 4A as detached from the bone pins in accordance with some embodiments of the disclosed subject matter.

FIG. 4A is a perspective view of yet another illustrative external fixator assembly in accordance with some embodiments of the disclosed subject matter. FIG. 4B is a perspective view of the external fixator assembly shown in FIG. 4A as detached from the bone pins in accordance with some embodiments of the disclosed subject matter. As shown in FIGS. 4A-4B, external fixator assembly 400 connects an aspect of humerus 401 and an aspect of ulna 403. This positioning is merely illustrative, and fixator assembly 400 may be positioned in any other suitable manner in accordance with the disclosed subject matter.

Fixator assembly 400 includes bone pins 402, 404, pin blocks 406, 408, and variable-linkage assembly 410. Bone pins 402, 404 and pin blocks 406, 408 may be positioned on and attached to the humerus and ulna in the same fashion as shown in the embodiment of FIG. 1. Variable linkage assembly 410 may be releasably coupled to pin blocks 406, 408 by locking mechanisms 416, 418 in the same fashion as shown in the embodiment of FIG. 1 (e.g., pins, screws or bolts).

Figure 4C:
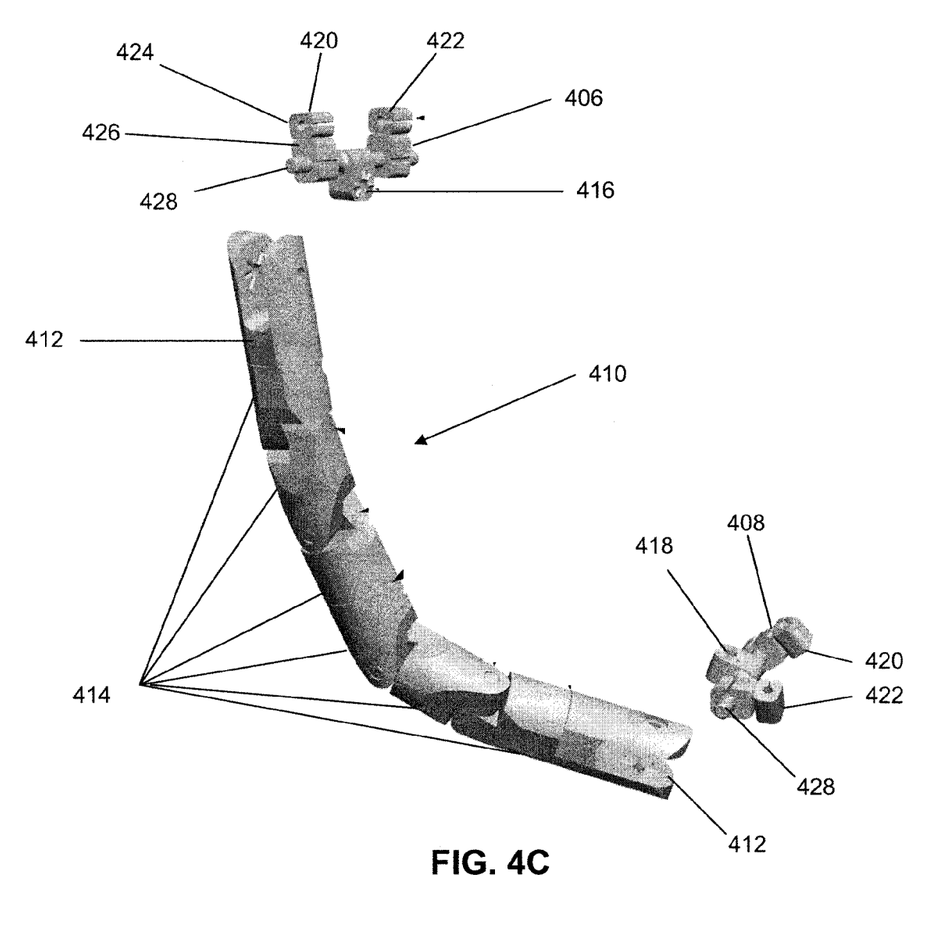
FIG. 4C is a perspective view of the external fixator assembly shown in FIGS. 4A and 4B illustrating pin blocks as disconnected from the assembly in accordance with some embodiments of the disclosed subject matter.

FIG. 4C is a perspective view of the external fixator assembly shown in FIGS. 4A and 4B illustrating pin blocks 406, 408 as disconnected from the assembly. As shown in FIG. 4C, pin blocks 406, 408 each include two pin connectors, 420, 422. Pin connectors 420, 422 each have a top part 424 and a bottom part 426. Top part 424 receives bone pins 402, 404, and is adjustably coupled to bottom part 426 such that top part 424 may pivot axially about bottom part 426. This flexibility allows pin blocks 406, 408 to accommodate the positioning and orientation of bone pins 402, 404. Bottom part 426 receives pin coupler 428 in order to link pin connectors 420, 422 to each other. After top part 424 has received bone pins 402, 404, and bottom part 426 has received pin coupler 428, connectors 420, 422 are locked into place.

As shown in FIG. 4C, variable-linkage assembly includes two arms 412 and multiple modular links 414. Arms 412 are releasably coupled at one end to pin blocks 406, 408 by locking mechanisms 416, 418 such that arms 412 can pivot three-dimensionally to accommodate the positioning and orientation of pin blocks 406, 408. Arms 412 are rotatably coupled at the other end to modular links 414.

Figure 4D:
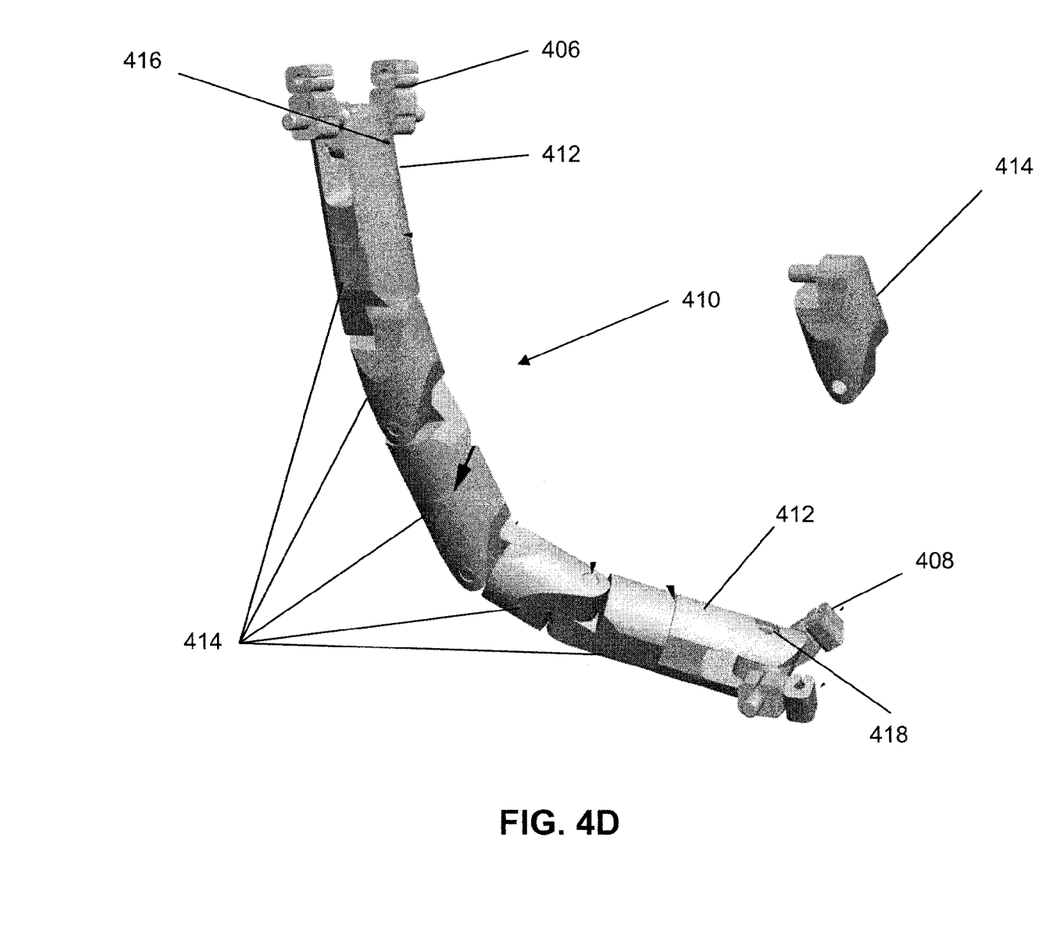
FIG. 4D is a perspective view of the external fixator assembly shown in FIGS. 4A and 4B illustrating a modular link as disconnected from the assembly in accordance with some embodiments of the disclosed subject matter.

FIG. 4D is a perspective view of the external fixator assembly shown in FIGS. 4A and 4B further illustrating a modular link of the assembly. As shown in FIG. 4D, modular links 414 are flexibly coupled to each other. In order to create a rigid construct of fixator assembly 400, the connections between pin blocks 406, 408 and arms 412, between arms 412 and modular links 414, and between the modular links, must be locked with respect to one another. In order to accommodate various spatial positions between pin blocks 406, 408, modular links 414 may be added or removed from variable-linkage assembly 410.

At time of rehabilitation, a surgeon or physical therapist can release variable-linkage assembly 410 at locking mechanisms 416, 418 in the same fashion as shown in the embodiment of FIG. 1. As with the embodiment of FIG. 1, rigidly locked variably-linkage assembly 410 can be released from locking mechanisms 416, 418 at pin blocks 406, 408 so that the joint can be unconstrained and mobilized in any direction. For example, the joint may be mobilized in a protected, supervised program by the surgeon or physical therapist. When the joint needs to be stabilized, the rigid variable-linkage assembly 410 is reattached to pin blocks 406, 408 in the original position obtained in the operating room using locking mechanisms 416, 418 in the same fashion as the embodiment shown in FIG. 1.

Figure 5:
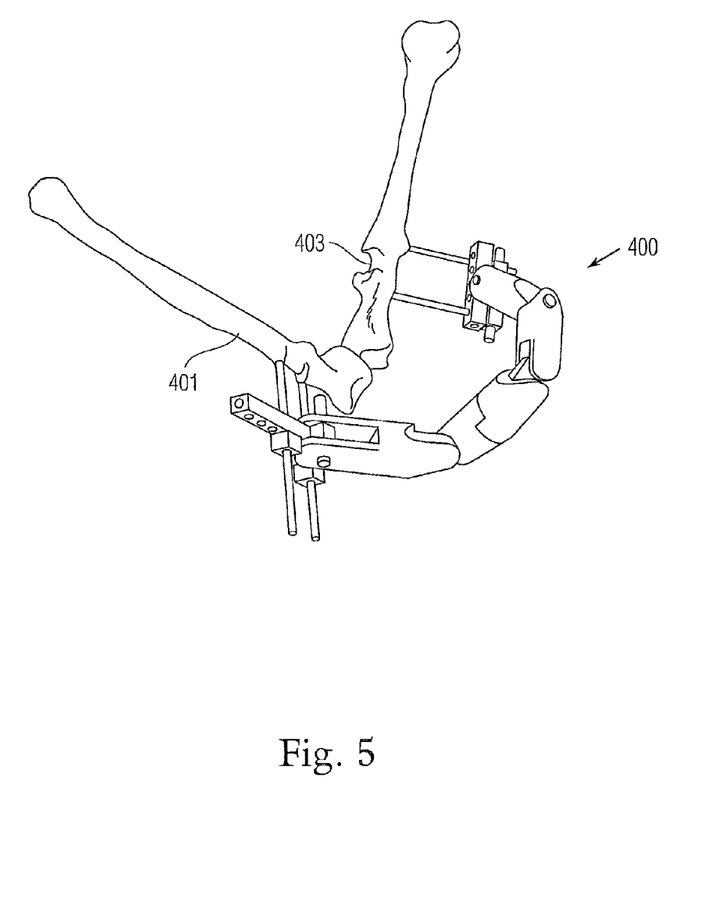
FIG. 5 is a perspective view of the external fixator assembly of FIG. 4A as applied in a different location and orientation in accordance with some embodiments of the disclosed subject matter.

FIG. 5 is a perspective view of the external fixator assembly of FIG. 4A as applied in a different location (e.g., safe zone) and orientation in accordance with some embodiments of the disclosed subject matter. FIG. 5, for example, shows an embodiment of fixator assembly 400 connecting different aspects of humerus 401 and ulna 403. As shown by FIG. 5, the external fixation device shown in FIG. 4 may be applied to various locations and in different configurations.

The following method may be used to apply the elbow fixator as disclosed herein to a patient, in accordance with some embodiments of the disclosed subject matter. This method is merely illustrative, and any other suitable method for applying the elbow fixator may be used in accordance with the disclosed subject matter. First, the injured elbow is taken to the operating room. The fracture and ligament repairs are made (or in some cases, prepared for repair). Second, bone pins are introduced into "safe zones" of the humerus and ulna, avoiding major peripheral nerves and the major muscle-tendon units of the elbow. Third, the pins are secured to a pin block. Fourth, the elbow is gently taken through a range of motion, assuring joint congruity and proper alignment. Fifth, once the proper joint position is determined, the humerus and ulna are linked with the variable-linkage assembly of the elbow fixation device disclosed herein. Sixth, ligament repairs are completed and the rest of the surgery finished. In some embodiments, x-ray confirmation of alignment could be used at this time.

The following post-operative method may be used for the elbow fixator, in accordance with some embodiments of the disclosed subject matter. This method is merely illustrative, and any other suitable post-operative method may be used in accordance with the disclosed subject matter. First, the patient is brought to a rehab area after dressing change. Second, the arm is placed in the "safe" overhead position, as illustrated, for example, in FIG. 3A. Third, fixator is unlinked. Range of motion is carried out as tolerated, under supervision. Fourth, the fixator is re-linked to maintain the static joint alignment that was achieved at the time of surgery.

A benefit of the external fixation device described herein includes simple application. The device does not require absolute identification of kinematic axis. The device provides for pin sites in "safe zones," as well as flexible pin placement. The device can be adaptable to existing bone fixation systems.

Another benefit of the external fixation device described herein includes simple operation and use. Once in place, the device can be unlinked for motion, and re-linked for joint protection. The device can be re-linked, for example, in the same position it was prior to unlinking, or in a different position. Re-linking the device in a different position would be performed, for example, by a surgeon. The device allows for a therapist or family member to disengage the frame for protected, limited motion during rehabilitation.

Yet another benefit of the external fixation device described herein includes unilateral or combined (e.g., medial and lateral) stabilization. A further benefit of the external fixation device described herein includes possible pin exchange due to, for example, infection.

Various clinical applications of the device described herein include, for example, acute trauma, interposition arthroplasty, adjunctive stabilization of reconstruction of ligaments, and adjunctive stabilization following contracture release.

The embodiments of the external fixation device disclosed herein are not limited to elbow applications and can be used with various other joints, e.g., a knee.

The device disclosed herein may be constructed at least in part of radiolucent material, for example. The assembly may be reusable in whole or in part. Alternatively, the assembly may be constructed for one-time use.

It will be understood that the foregoing is only illustrative of the principles of the invention, and that various modifications can be made by those skilled in the art without departing from the scope and spirit of the invention.

What is claimed is:

1. A device for external fixation of a joint, the joint having an anatomic pivot axis about which first and second skeletal elements are disposed, the device comprising:
   a first pin block for connection to the first skeletal element;
   a second pin block for connection to the second skeletal element; and
   a connection assembly for connection to the first and second pin blocks, wherein the connection assembly is releasably attached to at least one of the first and second pin blocks to allow the device to be locked in an original position when the connection assembly is attached to the first and second pin blocks, and to allow the device to be unlocked when the connection assembly is detached from at least one of the first and second pin blocks, wherein the connection assembly is formed of a plurality of parts that are coupled to one another and maintained in locked, fixed positions relative to one another when: (1) the connection assembly is attached to the device and the device is locked in the original position and also when: (2) the connection assembly is detached from the at least one of the first and second pin blocks, thereby allowing the device to be locked back into the original position, after detachment of the connection assembly from the at least one of the first and second pin blocks, by reattachment of the connection assembly to both the first and second pin blocks.

2. The device of claim 1, wherein the connection assembly comprises: first and second end portions coupled to the first and second pin blocks; and a linking member extending between and connected to the first and second end portions, the connections between the linking member and the first and second end portions each comprising a fastener to maintain the linking member in a fixed position with respect to the first and second pin blocks, wherein at least one of the connections is a releasable attachment, wherein when the connection assembly is detached from the at least one of the first and second pin blocks, the first and second end portions and linking member maintain a locked position relative to one another, thereby ensuring restoration of the original locked position when the connection assembly is reattached to both the first and second pin blocks.

3. The device of claim 2, wherein the releasable attachment between the linking member and the at least one of the first and second end portions comprises at least one screw configured to remain engaged to at least one of the first and second end portions following the release of the linking member from the at least one of the first and second end portions.

4. The device of claim 2, wherein the joint is rigidly constrained when the device is locked.

5. The device of claim 2, wherein the joint is unconstrained when the device is unlocked, the device being unlocked when the connection assembly is detached from the first and second pin blocks.

6. The device of claim 2, wherein the linking member is configured to accommodate a plurality of distances between the first and second pin blocks.

7. The device of claim 6, wherein the linking member includes a plurality of locking sites to accommodate the plurality of distances between the first and second pin blocks.

8. The device of claim 7, wherein at least one of the first and second end portions includes a plurality of locking sites to which one of the plurality of locking sites to which of the one locking sites of the linking member is releasably attached.

9. The device of claim 7, wherein the linking member is configured for reattachment to at least one of the first and second end portions at a selected locking site so that the device is locked in the original position.

10. The device of claim 1, wherein the connection assembly comprises: first and second end portions each releasably coupled to the first and second pin blocks, respectively, by a locking mechanism; and a linking member extending between and rotatably connected to the first and second end portions, the rotatable connections between the linking member and the first and second end portions each configured to maintain the linking member in a fixed position with respect to the first and second pin blocks when the device is locked.

11. The device of claim 10, wherein the linking member comprises an expandable linking member adapted to accommodate the distance between the first and second pin blocks.

12. The device of claim 10, wherein the linking member comprises a first curved member in sliding engagement with a second curved member, the sliding engagement between the first and second curved members allowing the linking member to adjust in size to accommodate the distance between the first and second pin blocks.

13. The device of claim 10, wherein the linking member comprises a plurality of plurality of modular linkages to accommodate the distance between the first and second pin blocks.

14. The device of claim 10, wherein the rotatable connections between the linking member and the first and second end portions comprise spherical ball joints.

15. The device of claim 10, wherein the first and second end portions are adapted for translation and rotation with respect to the first and second pin blocks.

16. A device for external fixation of a joint, the joint having an anatomic pivot axis about which first and second skeletal elements are disposed, the device comprising:
a first pin block for connection to the first skeletal element;
a second pin block for connection to the second skeletal element; and
a connection assembly for connection to the first and second pin blocks, the connection assembly comprising:
an end portion coupled to the first pin block, the end portion having a first planar engagement surface; and
a linking member coupled to the second pin block, the linking member having a second planar engagement surface that slidingly travels across the first planar engagement surface of the end portion to vary a position of the linking member relative to the end portion and permit the linking member to be fixedly locked into a first locked position selected from a plurality of different possible locked positions between the linking member and the end portion, wherein in each locked position, the linking member is connected to the end portion by a fastener which engages the linking member and the end portion,
wherein the linking member is releasably attached to the end portion to allow the device to be unlocked when the fastener is disengaged, whereby the first planar engagement surface is free to slide across the second planar engagement surface to allow the position of the linking member to change relative to the end portion.

17. The device of claim 16, wherein the linking member includes a plurality of locking sites to accommodate the distance between the first and second pin blocks.

18. The device of claim 16, wherein the linking member is configured to reattach to the end portion when the fastener is reengaged to lock the device back into the selected first locked position.

19. The device of claim 18, wherein each of the end portion and the linking member includes discrete, identifiable locking sites, with at least one locking site of the end portion being aligned with at least one locking site of the linking member in the selected first locked position for receiving the fastener for maintaining the device in the selected first locked position and permitting the device to be locked back into the selected first locked position after the alignment between the at least one locking site of the end portion and the at least one locking site of the linking member is restored and the linking member is reattached to the end portion.

20. A device for external fixation of a joint, the joint having an anatomic pivot axis about which first and second skeletal elements are disposed, the device comprising: a first pin block for connection to the first skeletal element; a second pin block for connection to the second skeletal element; and a connection assembly for connection to the first and second pin blocks, the connection assembly comprising: first and second end portions each releasably attached to the first and second pin blocks, respectively, by a locking mechanism to allow the connection assembly to be released from the first and second pin blocks; and a linking member extending between and rotatably connected to the first and second end portions, the rotatable connections between the linking member and the first and second end portions each configured to maintain the linking member in a fixed position with respect to the first and second pin blocks, wherein the connection assembly is releasably attached to the first and second pin blocks to allow the device to be locked in an original position when the connection assembly is attached to the first and second pin blocks, and to allow the device to be unlocked when the connection assembly is detached from the first and second pin blocks, wherein the joint is rigidly constrained when the device is locked, and the joint is unconstrained when the device is unlocked, and wherein the connection assembly is configured to reattach to the first and second pin blocks to lock the device in the original position.

21. The device of claim 20, wherein the linking member comprises a first curved member in sliding engagement with a second curved member, the sliding engagement between the first and second curved members allowing the linking member to adjust in size to accommodate the distance between the first and second pin blocks.

22. The device of claim 20, wherein the linking member comprises a plurality of modular linkages to accommodate the distance between the first and second pin blocks.

23. A device for external fixation of a joint having an anatomic pivot axis about which first and second skeletal elements are disposed, the device comprising:
- a first pin block for connection to the first skeletal element;
- a second pin block for connection to the second skeletal element;
- a connection assembly for connection to the first and second pin blocks, the connection assembly comprising:
  - an end portion coupled to the first pin block, the end portion having a plurality of discrete, individually identifiable first locking sites that are formed along a first engagement surface; and
  - a linking member coupled to the second pin block, the linking member having a plurality of discrete, individually identifiable second locking sites that are formed along a second engagement surface, wherein the first engagement surface slidingly travels along the second engagement surface to vary a distance between the first and second pin blocks and to permit the end portion and linking member to be locked into a first locked position selected out of a plurality of different locked positions that are defined between the end portion and the linking member, the selected first locked position being defined at least in part by a repeatable first alignment between at least one of the first locking sites and at least one of the second locking sites which allows a fastener to fixedly connect the linking member to the end portion and maintain the selected first locked position,
  - wherein the linking member is releasably attached to the end portion to allow the device to be unlocked when the fastener is disengaged, whereby the first engagement surface is free to slide across the second engagement surface to allow the position of the linking member to change relative to the end portion,
  - wherein the discrete and identifiable nature of each locking site of the first and second locking sites permit the linking member to be reattached to the end portion when the first alignment between the at least one of the first locking sites and the at least one of the second locking sites is restored and the fastener is reengaged between the linking member and the end portion.

24. The device of claim 23, wherein the first and second locking sites comprise discrete, individual openings spaced apart from one another and along the respective engagement surface.

25. The device of claim 23, wherein each of the first engagement surface and the second engagement surface comprises a planar surface to permit sliding movement between the end portion and the linking member.

26. The device of claim 24, wherein the fastener passes through aligned first and second locking sites for attaching the linking member to the end portion.

27. The device of claim 23, wherein the end portion is rotatably connected to the first pin block.

28. The device of claim 23, wherein the linking member comprises an arcuate shaped structure.

* * * * *